United States Patent
Morimoto

(10) Patent No.: US 9,869,612 B2
(45) Date of Patent: Jan. 16, 2018

(54) SUBSTRATE COLLECTING DEVICE

(71) Applicant: OLYMPUS CORPORATION, Tokyo (JP)

(72) Inventor: Nobuhiko Morimoto, Tokyo (JP)

(73) Assignee: Olympus Corporation, Tokyo (JP)

(*) Notice: Subject to any disclaimer, the term of this patent is extended or adjusted under 35 U.S.C. 154(b) by 160 days.

(21) Appl. No.: 14/695,108

(22) Filed: Apr. 24, 2015

(65) Prior Publication Data

US 2015/0226647 A1    Aug. 13, 2015

Related U.S. Application Data

(63) Continuation of application No. PCT/JP2013/077162, filed on Oct. 4, 2013.

(30) Foreign Application Priority Data

Oct. 24, 2012    (JP) .................................. 2012-234749

(51) Int. Cl.
*B32B 43/00*     (2006.01)
*G01N 1/04*     (2006.01)
(Continued)

(52) U.S. Cl.
CPC ............. *G01N 1/04* (2013.01); *B32B 43/006* (2013.01); *G01N 1/08* (2013.01); *G01N 1/312* (2013.01);
(Continued)

(58) Field of Classification Search
CPC ......... Y10T 156/1132; Y10T 156/1158; Y10T 156/1168; Y10T 156/1917;
(Continued)

(56) References Cited

U.S. PATENT DOCUMENTS 5,998,129 A * 12/1999 Schutze ................ B01L 3/0244
435/283.1
8,012,101 B2 * 9/2011 Lehtinen ............ A61B 10/0045
600/562
(Continued)

FOREIGN PATENT DOCUMENTS

JP         7-77657       3/1995
JP         11-148887     6/1999
(Continued)

OTHER PUBLICATIONS

International Search Report dated Nov. 12, 2013 received in related Application No. PCT/JP2013/077162, together with an English-language translation.

(Continued)

*Primary Examiner* — Mark A Osele
(74) *Attorney, Agent, or Firm* — Scully, Scott, Murphy & Presser, P.C.

(57) ABSTRACT

The present invention provides a substrate collecting device that includes a first stage on which a sheet is placed with a plurality of substrates facing downward, an sampler which carries out a predetermined operation on some of the substrates, which are disposed at predetermined positions, from above the first stage thereby to cause the substrates to come off from the sheet and fall, an optical system and a collector disposed below the first stage, and a second stage, which integrally moves the optical system and the collector in a horizontal direction. The second stage is capable of positioning the optical system and the collector at two positions at which the optical system or the collector is disposed substantially vertically below a predetermined position.

10 Claims, 7 Drawing Sheets

(51) Int. Cl.
  *G01N 1/08* (2006.01)
  *G02B 21/36* (2006.01)
  *G01N 1/31* (2006.01)
  *G01N 21/64* (2006.01)
  *B32B 41/00* (2006.01)

(52) U.S. Cl.
  CPC ....... *G01N 21/6456* (2013.01); *G02B 21/365* (2013.01); *B32B 41/00* (2013.01); *B32B 2310/0831* (2013.01); *G01N 2201/025* (2013.01); *Y10T 156/1158* (2015.01); *Y10T 156/1179* (2015.01); *Y10T 156/19* (2015.01); *Y10T 156/1917* (2015.01); *Y10T 156/1983* (2015.01)

(58) Field of Classification Search
  CPC ......... Y10T 156/1944; Y10T 156/1978; Y10T 156/1983; B32B 43/006; G01N 2201/025; G01N 1/04; G01N 1/08
  See application file for complete search history.

(56) References Cited

U.S. PATENT DOCUMENTS

2013/0084599 A1   4/2013  Morimoto
2014/0329269 A1*  11/2014  Adey ...................... G01N 1/04
                                                    435/30

FOREIGN PATENT DOCUMENTS

| JP | 2005-227113 A | 8/2005 | |
| WO | WO 8707911 A1 * | 12/1987 | ............... C12Q 1/24 |
| WO | WO 00/57153 A1 | 9/2000 | |
| WO | WO 03/010280 A1 | 2/2003 | |
| WO | WO 2011/149009 A1 | 12/2011 | |

OTHER PUBLICATIONS

European Extended Supplementary Search Report dated May 20, 2016 received in European Application No. 13 84 9192.3.

\* cited by examiner

SUBSTRATE COLLECTING DEVICE

CROSS-REFERENCE TO RELATED APPLICATIONS

The present application is a U.S. continuation application based on the PCT International Patent Application, PCT/JP2013/077162, filed on Oct. 4, 2013; the contents of which are incorporated herein by reference.

FIELD OF THE INVENTION

The present invention relates to a substrate collecting device.

BACKGROUND OF THE INVENTION

There has been known a device adapted to divide a glass substrate, to which a biological tissue section has been attached, together with the section in a state wherein the glass substrate has been attached to a sheet, and to collect some of the divided substrates together with section fragments, a desired substrate can be selectively collected by pushing, through the sheet, the back surface of the substrate facing downward thereby to cause the substrate to come off from the sheet and fall.

SUMMARY OF THE INVENTION

One aspect of the present invention provides a substrate collecting device that detaches and collects substrates among a plurality of substrates, which have been attached to a sheet such that the substrates can be detached by carrying out a predetermined operation, from the sheet, the substrate collecting device including: a first stage configured to move in a horizontal direction, the stage capable of holding a sheet, the sheet comprising a first surface and a plurality of substrates on a second surface, an optical system that observes one or more of the plurality of substrates on the stage, a collector that collects one or more of the plurality of substrates that is removed from the sheet, and a second stage that is capable of moving the optical system and the collector in the horizontal direction, wherein the second stage is configured to have a first position and a second position, the first position is such that the optical system is substantially vertically away from the second surface of the sheet and the second position is such that the collector is substantially vertically away from the second surface of the sheet. Furthermore, the substrate collecting device may conclude a sampler that is configured to cause at least one of the plurality of the substrates to be removed from the sheet.

According to one aspect of the present invention, the sheet to which the substrates have been attached is placed on the first stage, the position of the first stage is adjusted while observing a desired substrate by the optical system such that the substrate is disposed at a predetermined relative position with respect to the sampler, and the substrate disposed at the predetermined relative position is detached and dropped by the sampler, thereby allowing the desired substrate to be collected by the collector. Here, the positions of the optical system and the collector can be switched between the first position and the second position by the second stage, thereby allowing the optical system and the collector to be alternatively disposed substantially vertically below the first stage, while still adopting an inverted type optical design whereby to observe the substrate on the first stage through the optical system from below the first stage.

In this case, the movement range of the first stage is a sufficiently narrow range required for positioning a substrate relative to the sampler, so that the mechanism for moving the first stage has only to have a jogging function, thus permitting a simplified moving mechanism. Meanwhile, the accuracy for positioning the optical system and the collector relative to the sampler is not strictly required, as compared with that for the first stage, so that adequate positioning accuracy therefor can be achieved by the positioning carried out by the second stage.

In the aforesaid invention, the optical system may be provided with a reflector that reflects, at the first position, an image of at least one of the plurality of substrates the substrate on the first stage in a direction that intersects with a vertical direction, and a imaging sensor that acquires the image reflected by the reflector.

This arrangement enables the imaging sensor to acquire the image of the substrate, which is transmitted from the reflector, at an arbitrary position, so that the degrees of freedom of the disposition of the imaging sensor and the optical design can be increased. Further, the second stage is provided with the reflector, which is smaller and lighter than the imaging sensor, thus allowing the configuration of the second stage to be further simplified.

In the aforesaid invention, the substrates may be attached to the second surface of the sheet such that the substrates can be detached by being pushed from the first surface of the sheet, and the sampler may be provided with a pushing end that is configured to push the first surface of the sheet opposite at least one of the plurality of the substrates and a moving mechanism that moves the pushing end in the substantially vertical direction.

With this arrangement, some substrates disposed substantially vertically below the pushing end can be selectively detached from the sheet and dropped by a simple operation of merely moving the pushing member toward the substrates by the moving mechanism and pushing the substrates by the pushing end through the sheet.

In the aforesaid invention, the substrates may be attached to the sheet by an adhesive agent, the adhesive force of which is decreased by the irradiation of ultraviolet rays, and the sampler may have an emitting surface that irradiates ultraviolet rays to the predetermined relative position.

Thus, some substrates disposed at the predetermined relative position can be selectively detached from the sheet and dropped by a simple operation of merely emitting ultraviolet rays from the emitting surface.

DETAILED DESCRIPTION OF THE INVENTION

The following will describe a substrate collecting device 1 according to an embodiment of the present invention with reference to the accompanying drawings.

Figure 1:
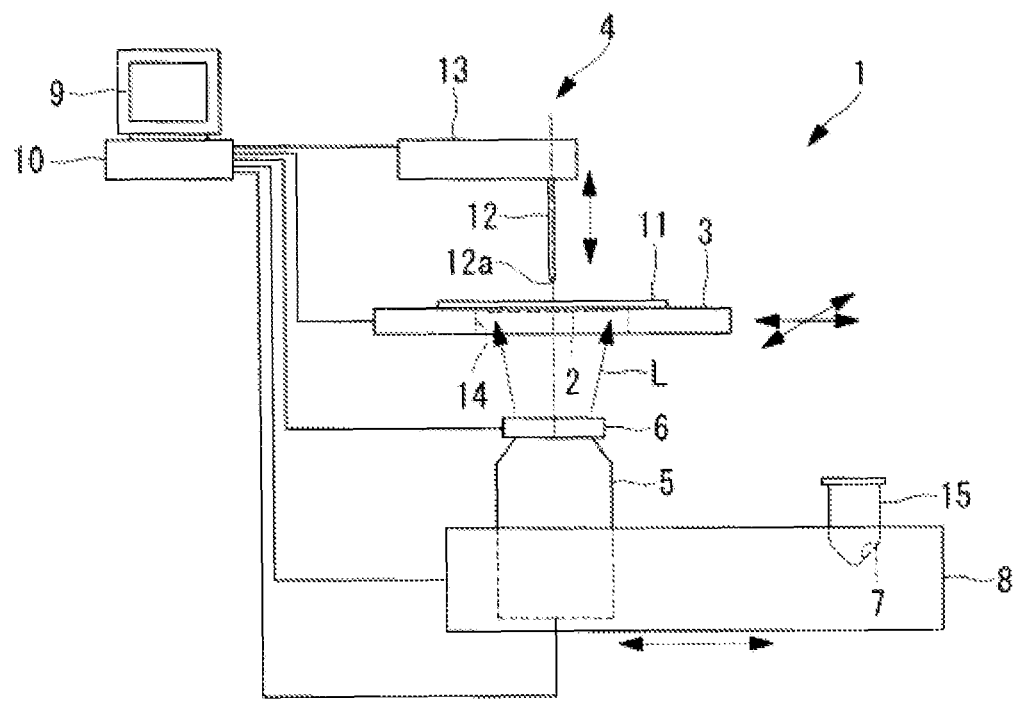
FIG. 1 is an entire configuration diagram of a substrate collecting device according to an embodiment of the present invention.

As illustrated in FIG. 1, the substrate collecting device 1 according to the present embodiment is provided with a substantially horizontal first stage 3 on which a substrate 2 is placed, an sampler 4 disposed above the first stage 3, an objective lens (optical system) 5 disposed below the first stage 3, an illuminating section 6, a collector 7, a moving unit (second stage) 8, which holds and integrally moves the objective lens 5, the illuminating section 6 and the collector 7, a display section 9 which displays an image observed through the objective lens 5, and a controller 10 which controls the first stage 3, the sampler 4, the illuminating section 6, and the moving unit 8.

Figure 2:
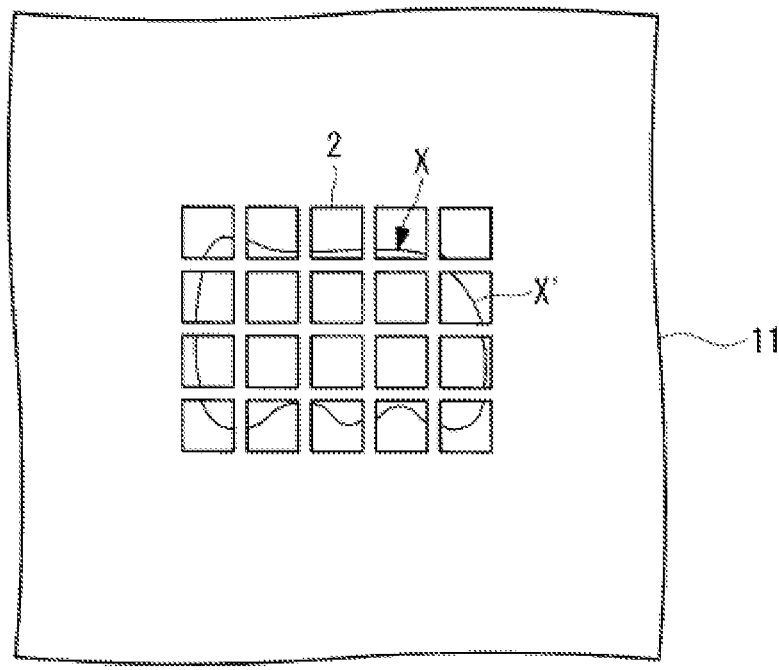
FIG. 2 is a diagram illustrating an example of substrates applied to the substrate collecting device of FIG. 1.

As illustrated in FIG. 2, a plurality of the substrates 2 are arranged with gaps thereamong on one surface of a sheet (sheet member) 11. A fragment X' of a section X cut out from a biological tissue is attached to the front surface of each of the substrates 2. The plurality of the substrates 2 are prepared by, for example, attaching an original substrate, such as a cover glass, which has the section X attached to the front surface thereof, to the sheet 11 and then cutting, dividing or breaking the original substrate together with the section X on the sheet 11. The shape and dimensions of each of the substrates 2 are not particularly restricted. For example, each of the substrates 2 is rectangular and has a thickness of 1 mm or less and a side dimension of 5 mm or less.

The back surface of each of the substrates 2 is detachably attached to the sheet 11 by an adhesive agent having an appropriate adhesive force. More specifically, the substrate 2 is attached to the sheet 11 with an adhesive force that allows the substrate 2 to come off from the sheet 11 when the back surface of the substrate 2 is pushed from the sheet 11 side with a force that is larger than the weight of the substrate 2 itself and that is equal to or larger than a predetermined magnitude. Further, the substrates 2 and the sheet 11 are optically transparent or translucent.

The sheet 11 is substantially horizontally placed on the first stage 3, which can be moved in the substantially horizontal direction. Further, the first stage 3 has a window 14 that penetrates in the direction of the thickness at the center thereof.

The sampler 4 has a thin and long, straight rod-shaped needle member (pushing member) 12 and a manipulator 13. The distal surface (pushing end) of the needle member 12 has a diameter dimension that is substantially equal to or less than the substrate 2. The manipulator 13 is capable of holding the needle member 12 with the distal end thereof facing substantially vertically downward and moving the needle member 12 in the substantially vertical direction. The manipulator 13 is adapted to move the needle member 12, which is held by the manipulator 13, in the vertical direction along the longitudinal direction thereof by being operated in the substantially vertical direction under the control by the controller 10.

The objective lens 5, the illuminating section 6 and the collector 7 are provided on the same moving unit 8. To be specific, the objective lens 5 is fixed to the moving unit 8 with the optical axis thereof set in the substantially vertical direction. Through the objective lens 5, the substrate 2 placed at the position of the window 14 of the first stage 3 is observed from below. The image formed by the objective lens 5 is displayed on the display section 9 through an optical system, which is not illustrated.

The illuminating section 6 is an annular lamp mounted on the distal surface of the objective lens 5 such that the lamp surrounds the distal surface and is composed of, for example, a white LED or an optical fiber. The illuminating section 6 irradiates illumination light L to the substrate 2 on the first stage 3 from below. The illuminating section 6 may be constructed to irradiate light that has an excitation wavelength of a fluorescent material contained in the section X to the substrate 2 as the illumination light L so that the fluorescence from the section X is observed through the objective lens 5.

The collector 7 is shaped as a hole which is formed in the moving unit 8 and which supports the bottom of a collecting container 15 shaped like a centrifugal tube.

The moving unit 8 is provided such that it can be moved in the horizontal direction by a direct acting guide, which is not illustrated. Further, the moving unit 8 is adapted to be positioned at two positions by a positioning mechanism, such as a click mechanism provided on the direct acting guide. More specifically, the moving unit 8 is provided such that it is alternatively positioned at a first position at which the optical axis of the objective lens 5 is disposed vertically below the needle member 12 and a second position at which the collector 7 is disposed vertically below the needle member 12. In FIG. 1, the moving unit 8 is disposed at the first position.

The controller 10 is adapted to control the operations of the first stage 3, the illuminating section 6, the moving unit 8 and the manipulator 13 in response to input operations by an operator. The operations the input to the controller 10 by the operator are carried out by using, for example, a user interface, which is provided on the controller 10 and which is not illustrated.

The operations of the first stage 3, the illuminating section 6, the moving unit 8, and the manipulator 13 may be controlled by the manual operations by the operator.

The operation of the substrate collecting device 1 constructed as described above will now be explained.

In order to collect some of the plurality of the substrates 2, which have been attached to the sheet 11, by the substrate collecting device 1 according to the present embodiment, the sheet 11 is first placed on the first stage 3. At this time, the sheet 11 is set on the first stage 3 such that the substrates 2 are disposed at the window 14 and also the substrates 2 are disposed on the bottom side of the sheet 11. A part of the sheet 11 may be fixed to the first stage 3 by a clip or the like such that the position of the sheet 11 is stabilized on the first stage 3.

Then, the operator disposes the moving unit 8 at the first position and turns on the illuminating section 6. Thus, the substrates 2 on the first stage 3 are observed through the objective lens 5 and the images of the substrates 2 are displayed on the display section 9. At this time, the substrates 2 and the sheet 11 are transparent or translucent and the section X attached to the substrate 2 is sufficiently thin, so that the needle member 12 disposed behind the sheet 11 relative to the objective lens 5 can be also observed through the objective lens 5.

Figure 3:
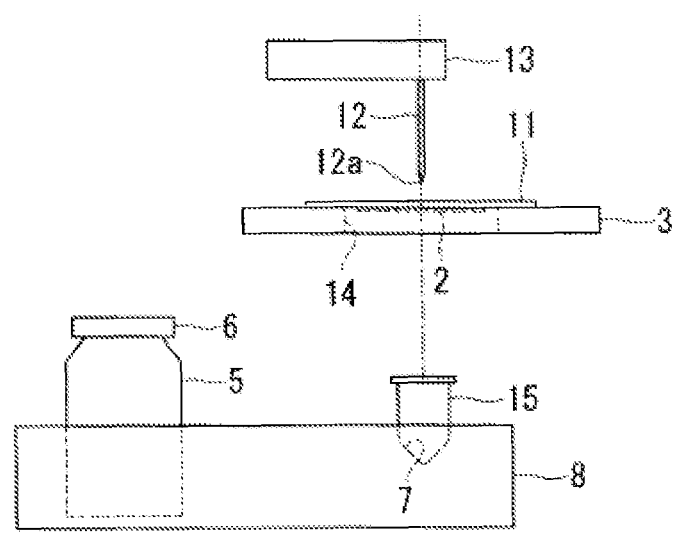
FIG. 3 is a partial configuration diagram of the substrate collecting device of FIG. 1, in which a moving unit is disposed at a second position.
Figure 4:
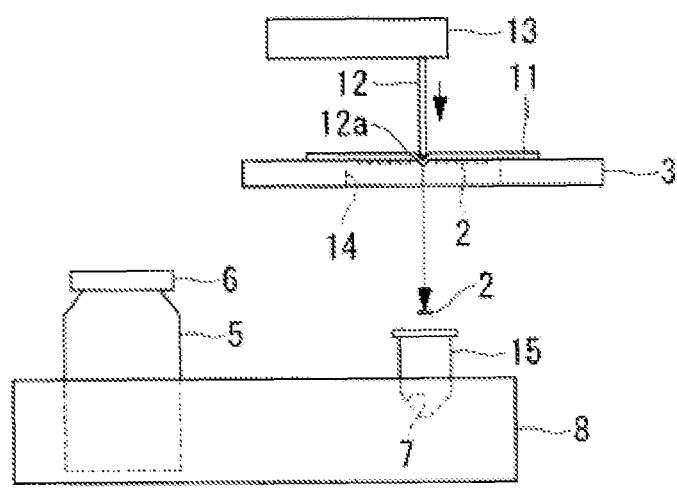
FIG. 4 is a partial configuration diagram illustrating an operation of the substrate collecting device of FIG. 1.

The operator adjusts the positions of the substrates 2 relative to the needle member 12 by moving the first stage 3 in the horizontal direction and the first stage 3 is positioned such that the one desired substrate 2 overlaps the distal surface of the needle member 12 in the image displayed on the display section 9. Subsequently, the operator moves the moving unit 8 to the second position to dispose the collecting container 15 located at the collector 7 at substantially vertically below the needle member 12, as illustrated in FIG. 3. Then, the operator operates the manipulator 13 downward to move the needle member 12 downward thereby to touch the distal surface of the needle member 12 against the back surface of the desired substrate 2, as illustrated in FIG. 4.

The substrate 2 pushed by the distal surface of the needle member 12 comes off from the sheet 11 and falls substantially vertically downward to be collected into the collecting container 15. To collect two or more substrates 2, the moving unit 8 is moved back to the first position, and the procedure from the step for positioning the first stage 3 to the step for pushing the substrate 2 by the needle member 12 is repeated.

As described above, the present embodiment makes it possible to both observe and collect the substrates 2 by alternatively placing the objective lens 5 and the collecting container 15 substantially vertically below the first stage 3 by switching the position of the moving unit 8 while still adopting by the inverted type optical design whereby to observe the substrates 2 on the first stage 3 from below the first stage 3 through the objective lens 5.

In this case, the movement range required of the first stage 3 is a sufficiently narrow range required for the positioning between the distal surface of the needle member 12 and the substrate 2. Hence, the moving mechanism of the first stage 3 may be provided with a jogging mechanism that moves with a minute travel distance within a relatively narrow movement range, thus making it possible to simplify the construction of the moving mechanism of the first stage 3.

The accuracy for positioning the first stage 3 relative to the needle member 12 and the substrate 2 is higher than the accuracy for positioning the objective lens 5 and the collector 7 relative to the needle member 12 and the substrate 2. Hence, for the objective lens 5 and the collector 7, positioning accuracy that is high enough for practical use can be achieved by a positioning mechanism, such as a click mechanism, even when the objective lens 5 and the collector 7 are moved for a relatively long distance by the moving unit 8.

In the present embodiment, the illuminating section 6 is adapted to be integrally moved by the moving unit 8 together with the objective lens 5 and the collector 7. Alternatively, however, the illuminating section 6 may be provided independently of the moving unit 8. For example, the illuminating section 6 may be fixed to the first stage 3.

With this arrangement, the substrates 2 on the first stage 3 can be illuminated by the illuminating section 6 at an arbitrary timing independently of the positional relationship between the objective lens 5 and the first stage 3.

Figure 5:
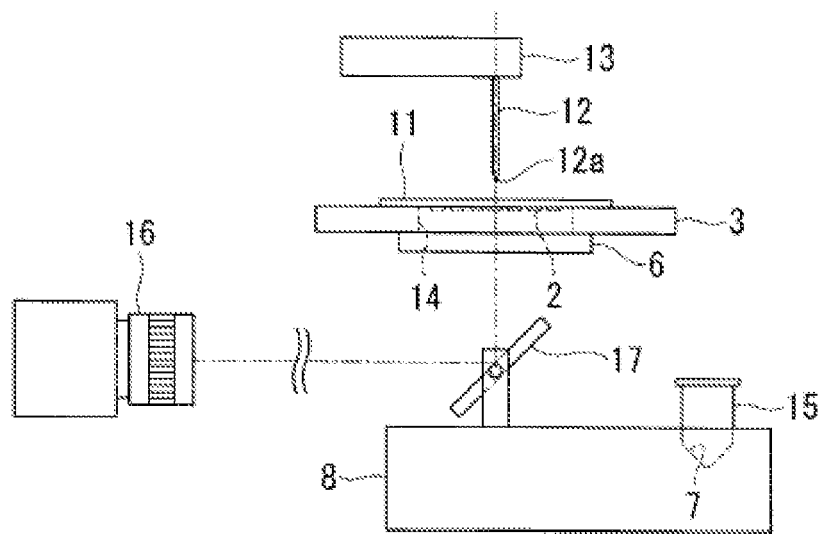
FIG. 5 is a partial configuration diagram illustrating a modified example of the substrate collecting device of FIG. 1.

Further, in the present embodiment, the objective lens 5 has been used as the means for observing the substrates 2. Alternatively, however, a camera (imaging sensor) 16 may be used. In this case, a mirror (reflector) 17 may be provided, which is fixed to a moving unit 8 and laterally reflects the image of a substrate 2 positioned at a window 14 at a first position and the camera 16 is disposed in the direction of reflection from the mirror 17, as illustrated in FIG. 5.

Transmitting the image of the substrate 2 on the first stage 3 to the camera 16 by the mirror 17 as described above makes it possible to provide the camera 16 independently of the moving unit 8, thus permitting a higher degree of freedom of the design of the camera 16. Further, the mirror 17 provided on the moving unit 8 is smaller and lighter than the objective lens 5 or the camera 16, so that the construction of the moving unit 8 can be simplified.

Further, in the present embodiment, the description has been given of the hole for accommodating the single collecting container 15 as the collector 7; however, the configuration of the collector 7 is not limited thereto. The collector may be a groove in which a microplate having a plurality of holes is installed. Further, the collector may be formed of a member having adhesiveness to capture the falling substrates 2 by the adhesiveness.

Further, a moving unit 8 may be provided with a plurality of collectors 7 and the moving unit 8 may be constructed such that the moving unit 8 can be positioned at three or more positions at which the individual collectors 7 are disposed substantially vertically below needle members 12. Further, the moving unit 8 may be rotatively moved.

Figure 6:
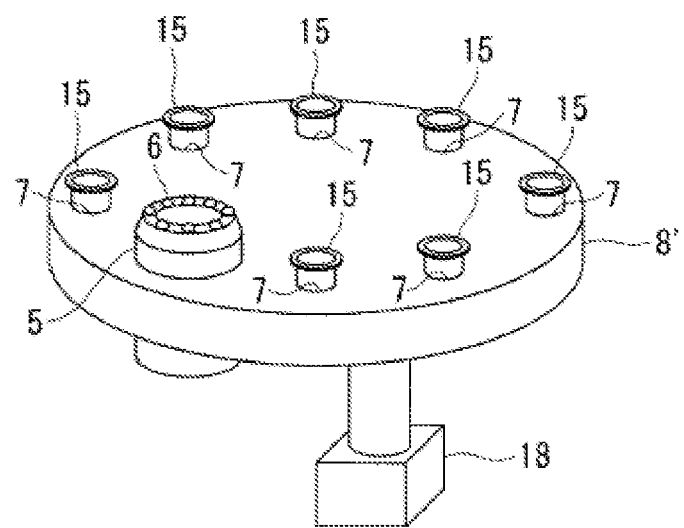
FIG. 6 is a partial configuration diagram illustrating another modified example of the substrate collecting device of FIG. 1.

FIG. 6 illustrates a disc shaped moving unit 8'. The moving unit 8' has a plurality of (seven in the illustrated example) collectors 7, each of which is formed of a hole into which the bottom of a collecting container 15 is inserted, the collectors 7 being arranged in the circumferential direction. Reference numeral 18 denotes a stepping motor that rotates the moving unit 8' in the circumferential direction. The stepping motor 18 rotates the moving unit 8' in steps such that an objective lens 5 and the plurality of the collecting containers 15 inserted in the collectors 7 are alternatively positioned substantially vertically below a needle member 12.

This arrangement also makes it possible to alternatively position the objective lens 5 and the collecting containers 15 substantially vertically below the needle member 12 by the moving unit 8'.

Further, in the present embodiment, the sampler 4 is provided with the needle member 12; however, the construction of the sampler 4 is not limited thereto. For example, the sampler 4 may be provided with a tubular member in place of the needle member 12. Further, the needle member 12 may be inserted in the tubular member such that the distal end of the needle member 12 juts out.

Further, a plurality of needle members 12 may be bundled and held by the manipulator 13, or a crown needle having the distal portion thereof split into a plurality of ends may be used as the needle member 12. In the case where the sampler 4 has the needle member 12 with a plurality of distal surfaces as described above, the sampler 4 may be constructed such that a plurality of the substrates 2 are simultaneously pushed by the plurality of the distal surfaces of the needle member 12 to detach and drop the substrates 2.

Figure 7:
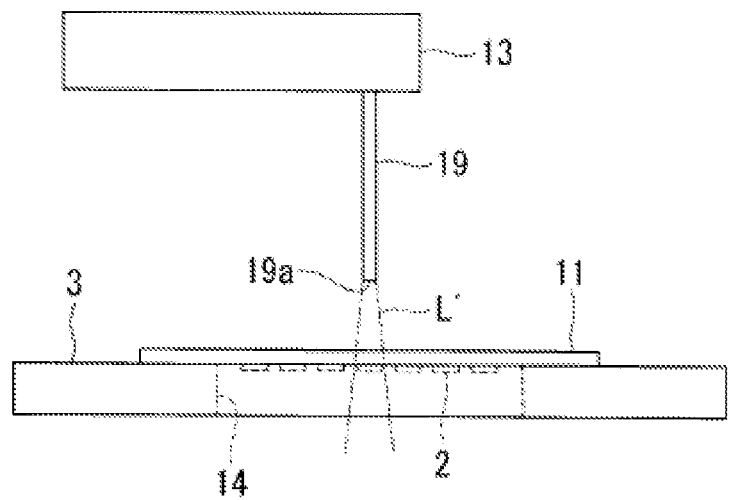
FIG. 7 is a partial configuration diagram illustrating yet another modified example of the substrate collecting device.

Further, in place of the needle member 12, an optical fiber 19 having a small-diameter distal surface (emitting surface) 19a, as illustrated in FIG. 7, may be used. In this case, an ultraviolet peeling type adhesive agent, the adhesive force of which decreases when exposed to light of a particular wavelength, e.g. ultraviolet light, is used as the adhesive agent for bonding substrates 2 to a sheet. Then an ultraviolet ray L' is irradiated to the sheet 11 from the distal surface 19a of the optical fiber 19, and the substrate 2 to which the ultraviolet ray L' has been irradiated is pushed by the optical fiber 19 as necessary and comes off from the sheet 11 and falls. At this time, the dimensions of the distal surface 19a, the emitting angle of the ultraviolet ray L' from the distal surface 19a, the distance between the distal surface 19a and the first stage 3, and the like are set such that the ultraviolet ray L' is irradiated to only the desired substrate or substrates among a plurality of substrates 2 bonded to the sheet 11.

DESCRIPTION OF REFERENCE NUMERALS 1 substrate collecting device
2 substrate 3 first stage
4 sampler
5 objective lens (optical system)
6 illuminating section
7 collector
8 second stage
9 display section
10 controller
11 sheet (sheet member)
12 needle member (pushing member)
12a distal surface (pushing end)
13 manipulator
14 window
15 collecting container
16 camera (optical system, imaging sensor)
17 mirror (optical system, reflector)
18 stepping motor
19 optical fiber
19a distal surface (emitting surface)
X section
X' fragment

The invention claimed is:

1. A substrate collecting device, comprising:
a first stage configured to move in a horizontal direction, the stage capable of holding a sheet, the sheet comprising a first surface and a plurality of substrates on a second surface;
an optical system that observes one or more of the plurality of substrates on the stage;
a container that collects one or more of the plurality of substrates that is removed from the sheet;
a second stage, wherein the second stage is configured to move the optical system and the container in the horizontal direction, wherein the second stage is configured to have a first position and a second position, the first position is such that the optical system is substantially vertically away from the second surface of the sheet and the second position is such that the container is substantially vertically away from the second surface of the sheet; and
a sampler that is configured to cause at least one of the plurality of the substrates to be removed from the sheet, wherein the sampler comprises a pushing end that is configured to push the first surface of the sheet opposite at least one of the plurality of the substrates, and wherein the sampler is configured to move in a substantially vertical direction, wherein the second stage is disposed a vertical distance from the sampler that is larger than a vertical distance between the first stage and the sampler, wherein the first stage is vertically between the second stage and the sampler, and wherein the second stage is configured to hold the optical system and the container.

2. The substrate collecting device according to claim 1, wherein the optical system comprises:
a reflector that reflects, at the first position, an image of at least one of the plurality of substrates on the first stage; and
a imaging sensor that acquires the image reflected by the reflector.

3. The substrate collecting device according to claim 1, wherein each of the plurality of the substrates are attached to the sheet, and each of the plurality of the substrates are configured to be detached from the second surface of the sheet by being pushed from the first surface of the sheet.

4. The substrate collecting device according to claim 1, wherein each of the plurality of substrates are attached to the sheet by an adhesive agent, wherein the adhesive force of the adhesive agent is decreased by irradiation of ultraviolet rays, and
wherein the sampler has an emitter that irradiates the ultraviolet rays to the adhesive agent of at least one of the plurality of the substrates.

5. The substrate collecting device according to claim 1, wherein each of the plurality of substrates is rectangular.

6. The substrate collecting device according to claim 1, wherein the container is formed in the second stage.

7. The substrate collecting device according to claim 6, wherein the container is a groove.

8. The substrate collecting device according to claim 1, wherein the container is formed of an adhesive on the second stage.

9. The substrate collecting device according to claim 1, wherein the second stage is configured to have three or more positions.

10. The substrate collecting device according to claim 1, wherein the second stage is configured to rotate to move the optical system and the container in the horizontal direction.

* * * * *